(12) United States Patent
Hall et al.

(10) Patent No.: US 11,877,731 B2
(45) Date of Patent: Jan. 23, 2024

(54) TOILET WITH INTEGRAL MICROSCOPE SLIDE

(71) Applicant: Medic, Inc., Provo, UT (US)

(72) Inventors: David R. Hall, Provo, UT (US); Jared Reynolds, Spanish Fork, UT (US); Jared Blake, Orem, UT (US); Joshua Larsen, Spanish Fork, UT (US)

(73) Assignee: Hall Labs LLC, Provo, UT (US)

( * ) Notice: Subject to any disclaimer, the term of this patent is extended or adjusted under 35 U.S.C. 154(b) by 500 days.

(21) Appl. No.: 17/195,569

(22) Filed: Mar. 8, 2021

(65) Prior Publication Data

US 2021/0275153 A1    Sep. 9, 2021

Related U.S. Application Data

(60) Provisional application No. 62/986,655, filed on Mar. 7, 2020.

(51) Int. Cl.
| | | |
|---|---|---|
| *A61B 10/00* | (2006.01) | |
| *A47K 13/24* | (2006.01) | |
| *G01N 33/487* | (2006.01) | |

(52) U.S. Cl.
CPC .......... *A61B 10/007* (2013.01); *A47K 13/24* (2013.01); *A61B 10/0038* (2013.01); *G01N 33/4875* (2013.01)

(58) Field of Classification Search
CPC .............. A61B 10/007; A61B 10/0038; A61B 10/0045; A47K 13/24; G01N 33/4875
See application file for complete search history.

(56) References Cited

U.S. PATENT DOCUMENTS

| | | | | |
|---|---|---|---|---|
| 2013/0029407 | A1* | 1/2013 | Terazono | G01N 21/6408 |
| | | | | 435/287.2 |
| 2014/0273068 | A1* | 9/2014 | Wanders | G01N 15/1404 |
| | | | | 435/29 |
| 2018/0371735 | A1* | 12/2018 | Hall | A61B 5/1455 |

* cited by examiner

*Primary Examiner* — Suman K Nath

(57) ABSTRACT

An analytical toilet comprising a bowl adapted to receive excreta; a channel in fluid communication with the bowl for extracting a sample of excreta from the bowl; an imaging section in the channel, comprising a transparent window; and a movable wall capable of moving between a first and a second position; wherein the channel is open when the movable wall is in a first position; and wherein the channel is nearly closed when the movable wall is in a second position; a first actuator adapted to move the movable wall between its first and second position; an imaging sensor positioned to image the contents of the channel at the point of the movable wall through the transparent window is disclosed.

19 Claims, 2 Drawing Sheets

TOILET WITH INTEGRAL MICROSCOPE SLIDE

CROSS-REFERENCE TO RELATED APPLICATIONS

This application claims priority to U.S. Patent Application No. 62/986,655 titled "Toilet Manifold with Integral Microscope Slide" filed on 7 Mar. 2020, which is incorporated herein by reference in its entirety.

TECHNICAL FIELD

The present disclosure relates to toilets. More particularly, it relates to analytical toilets equipped to provide health and wellness information to a user.

BACKGROUND

The ability to track an individual's health and wellness is currently limited to the lack of available data related to personal health. Many diagnostic tools are based on examination and testing of excreta, but the high cost of frequent doctor's visits and/or scans make these options available only on a very limited and infrequent basis. Thus, they are not widely available to people interested in tracking their own personal wellbeing.

Toilets present a fertile environment for locating a variety of useful sensors to detect, analyze, and track trends for multiple health conditions. Locating sensors in such a location allows for passive observation and tracking on a regular basis of daily visits without the necessity of visiting a medical clinic for collection of samples and data. Monitoring trends over time of health conditions supports continual wellness monitoring and maintenance rather than waiting for symptoms to appear and become severe enough to motivate a person to seek care. At that point, preventative care may be eliminated as an option leaving only more intrusive and potentially less effective curative treatments. An ounce of prevention is worth a pound of cure.

Just a few examples of smart toilets and other bathroom devices can be seen in the following U.S. Patents and Published Applications: U.S. Pat. No. 9,867,513, entitled "Medical Toilet With User Authentication"; U.S. Pat. No. 10,123,784, entitled "In Situ Specimen Collection Receptacle In A Toilet And Being In Communication With A Spectral Analyzer"; U.S. Pat. No. 10,273,674, entitled "Toilet Bowl For Separating Fecal Matter And Urine For Collection And Analysis"; US 2016/0000378, entitled "Human Health Property Monitoring System"; US 2018/0020984, entitled "Method Of Monitoring Health While Using A Toilet"; US 2018/0055488, entitled "Toilet Volatile Organic Compound Analysis System For Urine"; US 2018/0078191, entitled "Medical Toilet For Collecting And Analyzing Multiple Metrics"; US 2018/0140284, entitled "Medical Toilet With Customized Health Metric Validation System"; US 2018/0165417, entitled "Bathroom Telemedicine Station." The disclosures of all these patents and applications are incorporated by reference in their entireties.

One thing that is commonly done to fecal samples is viewing them under a microscope. This can help identify parasite larvae and eggs, bacteria, viruses, blood and other microscopic features. Current technology does not provide a way to automate viewing and imaging liquified feces with a microscope in a toilet system.

SUMMARY

In a first aspect, the disclosure provides an analytical toilet comprising a bowl adapted to receive excreta; a channel in fluid communication with the bowl for extracting a sample of excreta from the bowl; an imaging section in the channel, comprising a transparent window; and a movable wall capable of moving between a first and a second position; wherein the channel is open when the movable wall is in a first position; and wherein the channel is nearly closed when the movable wall is in a second position; a first actuator adapted to move the movable wall between its first and second position; an imaging sensor positioned to image the contents of the channel at the point of the movable wall through the transparent window.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 1:
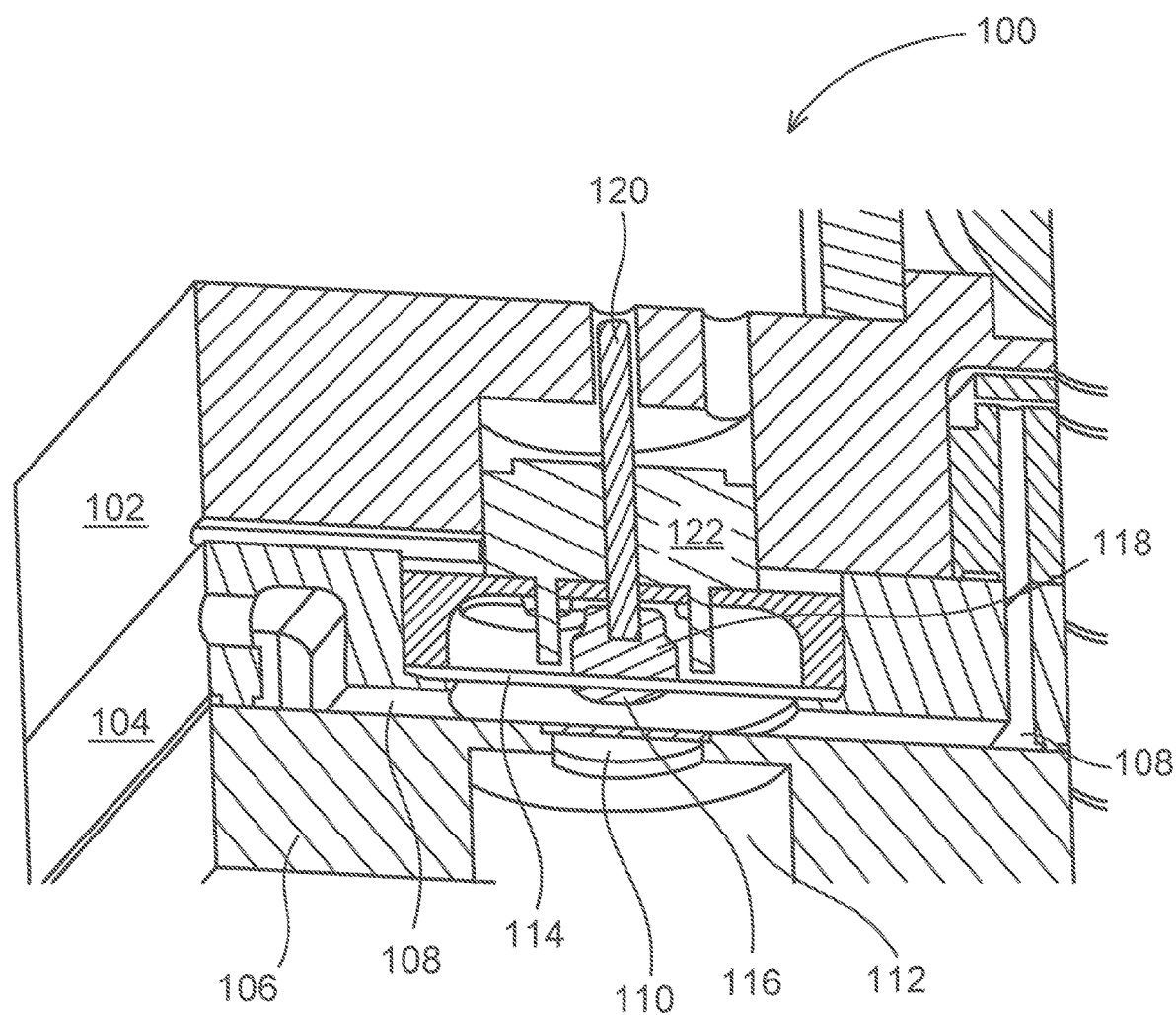
FIG. 1 illustrates a cross-sectional view of a portion of a manifold system in an analytical toilet, according to an embodiment of the disclosure.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, the term "excreta" refers to any substance released from the body including urine, feces, menstrual discharge, and anything contained or excreted therewith. The term "solid excreta" specifically refers to feces, even when the feces is in a more liquid or watery state, as when a user is suffering from diarrhea or gastroenteritis.

As used herein, "toilet" is meant to refer to any device or system for receiving human excreta, including urinals.

As used herein, the term "bowl" refers to the portion of a toilet that is designed to receive excreta.

As used herein, the term "base" refers to the portion of the toilet below and around the bowl supporting it.

As used herein, the term "user" refers to any individual who interacts with the toilet and deposits excreta therein.

As used herein, the term "manifold" is intended to have a relatively broad meaning, referring to a device with multiple conduits and valve to controllably distribute fluids, namely water, liquid sample and air.

As used herein, the term "comminute" is meant to have a relatively broad meaning, referring to the process of making smaller pieces out of bigger pieces. In the context of the present invention, the feces deposited in the toilet can be comminuted by various methods so as to make it easier to analyze and/or further process.

Exemplary Embodiments

The present disclosure relates to an analytical toilet used to examine excreta for health and wellness indicators. One problem with attempting to examine feces in a toilet environment is preparing a thin sample (i.e., the space between glass slides typically used with microscopes) that can be imaged with a microscope camera. The present disclosure provides a flow path that is converted into a microscope slide by compressing a flexible wall into a transparent (e.g., glass) wall on the opposite side of the flow path. This creates a space in the flow path that mimics the conditions in a slide for microscopy for detection of foreign materials.

In various exemplary embodiments, the analytical toilet includes a manifold system designed to provide flow of multiple fluids through a variety of analytical test centers designed to image and/or test excreta for a variety of purposes using a variety of methods. The fluids in the manifold may include, among others, urine, feces, water, reagents, dyes, cleansers, diluents, cleansers, and rinse solutions.

In a first process, the feces may need to be comminuted to form a slurry in order to be capable to flow through the manifold system. This may include adding a first fluid, such as water, followed by a comminution method. A first fluid may comprise water, buffers, reagents, dyes, cleansers, diluents, cleansers, rinse solutions or combinations thereof. Such comminution methods may include using an auger, masticating auger, emulsification, sonication, acoustic wave actuator, vibrating mill, high pressure fluid grinding, waring blender, Dounce homogenizer, Potter-Elvehjem homogenizer, French press, or a mechanical grinder.

FIG. 1 illustrates a cross-sectional view of a portion of a manifold system in an analytical toilet, according to an embodiment of the disclosure. Flow containing liquified feces is directed into a channel with a moveable wall, such as a flexible diaphragm, and a transparent window. The window may be part of the moveable wall or another side of the channel at the same section as the moveable wall. The window may comprise glass, which may also be a lens to magnify the contents of the channel for an imaging sensor. The moveable wall may have a portion that comprises glass. A linear actuator, such as a piston or solenoid, is used to press the moveable wall into the channel mimicking the conditions between two glass slides. In a preferred embodiment, the moveable wall is a flexible diaphragm, is transparent, or has an opening to allow light to pass, and a light source is provided to illuminate the sample being imaged. In a preferred embodiment, the light source is located on or in a solenoid plunger used to compress the flow channel.

FIG. 2 illustrates a flow channel in a manifold system 100, according to an embodiment of the disclosure. Manifold system 100 comprises a first manifold layer 102, second manifold layer 104 and a third manifold layer 106. Manifold system 100 comprises a flow path 108 for the sample to be tested, such as comminuted feces in slurry form. Flow channel 108 comprises an inlet and outlet and is in fluid communication with a bowl to receive excreta from a user.

Manifold system 100 further comprises a microscope lens 110 and a cavity for an imaging sensor 112 (microscope not shown). Microscope lens 110 may be a glass plate, magnifying lens or a microscope slide. System 100 further comprises a membrane or diaphragm 114. In an exemplary embodiment, diaphragm 114 is flexible. Diaphragm 114 may comprise a polymer. Diaphragm 114 may comprise a rubber or an elastomer such as a silicone-based polymer.

Diaphragm 114 comprises a window 116. A window 116 may be substantially transparent. Window 116 is adjacent a light source 118 such that light may pass through window 116. Light source 118 further comprises a tube or other passageway 120 to allow for electrical power to be supplied to the light source 118. Tube 120 may also act as a plunger or piston in an actuator system. Manifold system 100 further comprises an actuator system 122. Actuator system 122 is preferably a linear actuator system such that the actuator system 122 deforms the diaphragm 114 in a direction towards microscope lens 110. Actuator system 122 may be a solenoid, hydraulic, pneumatic, electric, thermal, magnetic, coiled polymer, supercoiled polymer or other mechanical-based actuator.

Figure 2A:
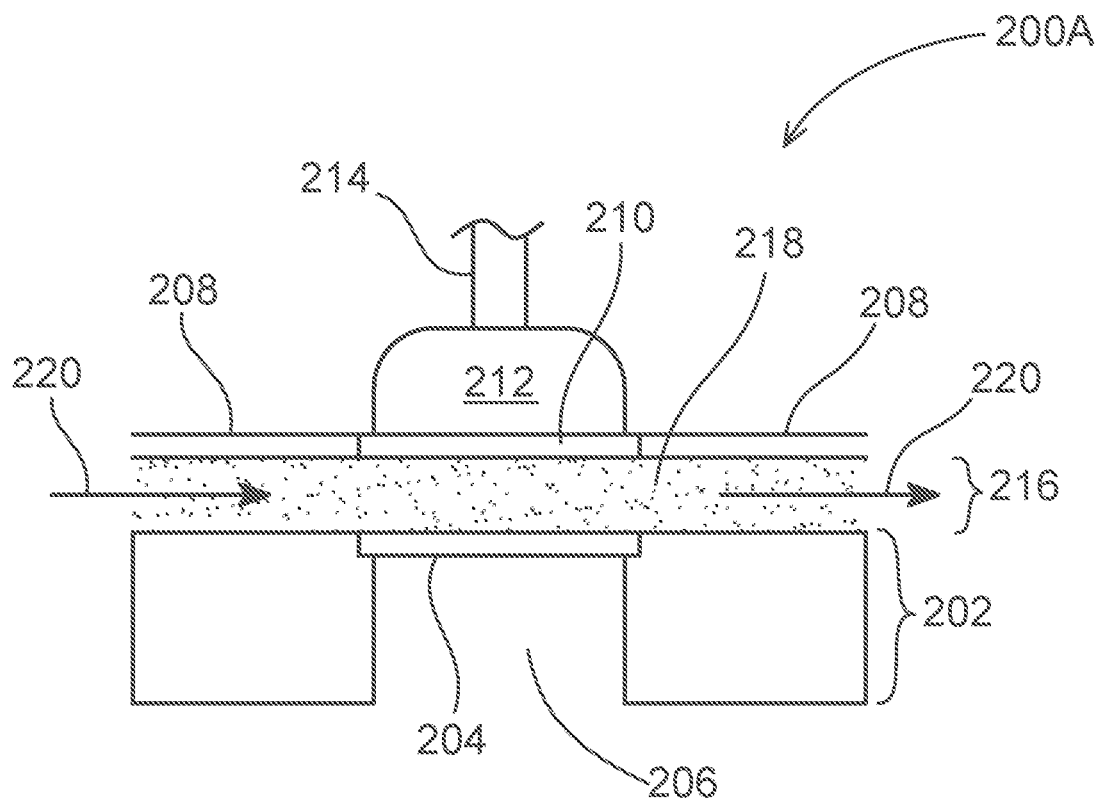
FIG. 2A is a view of the flow path in an open position in a portion of a manifold system, according to an embodiment of the disclosure.

FIG. 2A is a view of the flow channel in an open position in a portion of a manifold system 200A, according to an embodiment of the disclosure. The portion of manifold system 200A in FIG. 2A shows a manifold layer 202, microscope lens 204, imaging sensor cavity 206, diaphragm 208, diaphragm opening 210, light source 212 and power source 214. In illustration 200A, the flow channel 216 is shown to be in an open position. Flow of the comminuted feces slurry 218 occurs within flow channel 216 and the directional flow is shown by arrows 220. In this state the diaphragm 208 is not stretched. Flow channel 216 comprises an inlet and outlet and is in fluid communication with a bowl to receive excreta from a user.

Figure 2B:
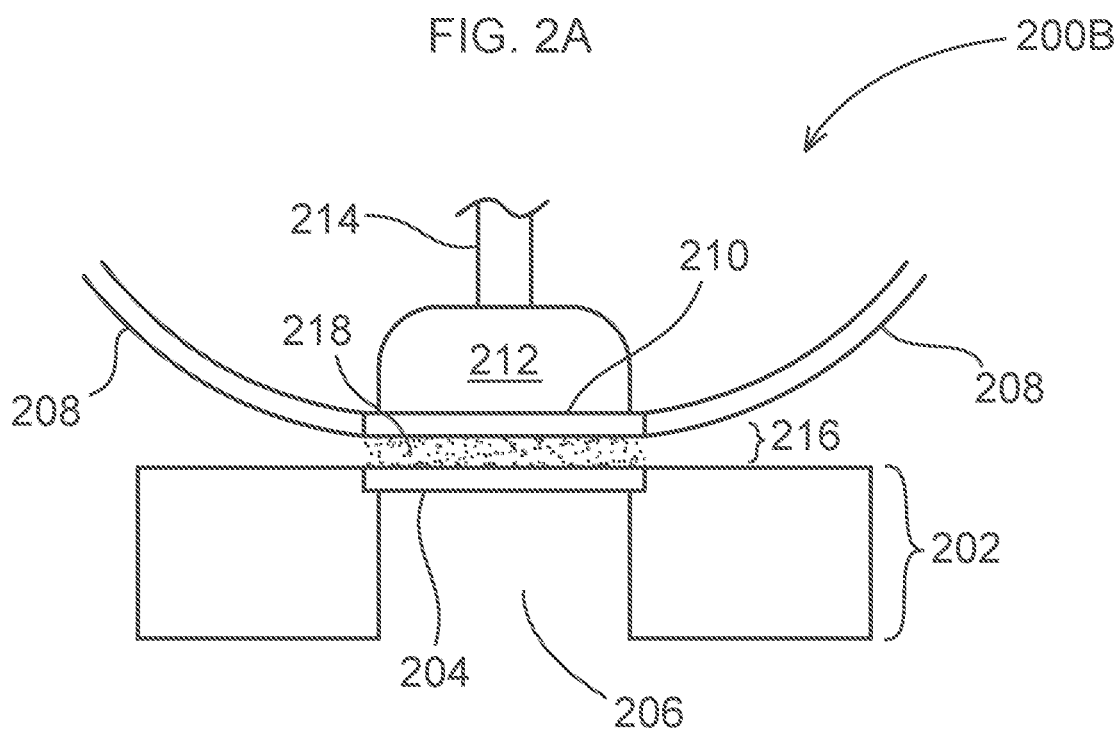
FIG. 2B is a view of the flow path in a closed position in a portion of a manifold system, according to an embodiment of the disclosure.

FIG. 2B is a view of the flow channel in a closed position in a portion of a manifold system 200B, according to an embodiment of the disclosure. In this state, the flexible diaphragm 208 is pressed against the microscope lens 204. When flow channel 216 is compressed and narrowed, a thin layer of fluid, such as comminuted feces, is trapped between the flexible membrane 208 and the microscope lens 204. An imaginf sensor may be located behind the lens 204 in cavity 206 in order to view and/or take images (still images or video) of the comminuted feces. The imaging sensor may be controlled automatically or may be manually controlled. Images may be viewed real time or recorded for later examination. In various embodiments, either the microscope lens 204 or the flexible membrane 208 may be placed above the flow channel 216. The microscope lens 204 and the flexible diaphragm 208 may also be placed to the sides of the flow channel 216.

In various exemplary embodiments, the actuator system 122 is adapted to narrow the flow path channel 108, 216 without entirely closing the channel. The flow path channel 108, 216 should be narrowed enough to compress feces between the surfaces without forcing the feces out of the narrowed portion of the channel. This is intended to mimic the conditions between two conventional slides used with microscopes in a conventional laboratory setting. This may make it easier to detect foreign material such as parasitic, bacterial and viral-based material. Microscopic methods such as bright field microscopy, oblique illumination, dark field microscopy, dispersion staining, phase contrast microscopy, differential interference contrast microscopy, interference reflection microscopy, fluorescence microscopy, confocal microscopy, light sheet fluorescence microscopy, wide-field multiphoton microscopy, serial time-encoded amplified microscopy or X-ray microscopy.

An image inspection system may be used to detect abnormalities in a sample of comminuted feces. An image system may comprise a transducer. Some image inspection systems may include KEYENCE (Itasca, IL, USA), INSPECT.assembly™ (Radiant Vision Systems, Redmond, WA, USA) or Lake Image Systems (Tring, Hertfordshire, United Kingdom). An image inspection sensor provides a visual sensor for the presence of parasites, blood, consistency, etc. An image inspection system may comprise one or more cameras and may provide 2D or 3D images. The image system may incorporate optical lenses for magnification of the sample, and light sources to supply illumination from above or below the sample. The image system may incorporate various optical filters to enhance the visibility of sample targets, or specific features of interest. The image system may detect movement, such as from a living parasite. Such parasites may include protozoan (i.e., single-celled parasites), such as cryptosporidium, microsporidia, and isospora. The parasites may also include parasitic worms (helminths), such as tapeworms, flukes, *Fasciolopsis buski*, hookworms, microsporidia, whipworms, protozoa, *Balantidium coli, Dientamoeba fragilis, Encephalitozoon hellem, Necator americanus, Heterophyes heterophyes, Metagonimus yokogawai*, pinworms, trichinosis worms, *Giardia intestinalis, Giardia lamblia, Entamoeba histolytica, Cyclospora cayetanenensis*, ascarias *lumbricoides*, strongyloidiasis, *Ancylostoma duodenale, Taenia, Cystoisospora belli, Diphyllobothrium, Hymenolepsis, Echinococcus, Dipylidium, Spirometra, Enterobius vermicularis* and *Cryptosporidium*. The image system may also be able to detect the eggs of one or more parasites.

In some instances, the image system may also detect toxins from bacteria such as *Clostridium difficile*. In some instances, the image system may also detect viruses such as rotovirus.

All patents, published patent applications, and other publications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:

1. An analytical toilet comprising:
a bowl adapted to receive excreta;
a channel in fluid communication with the bowl for extracting a sample of excreta from the bowl;
an imaging section in the channel, comprising:
a transparent window; and
a movable wall capable of moving between a first and a second position;
wherein the channel is open when the movable wall is in a first position; and
wherein the channel is nearly closed when the movable wall is in a second position;
a first actuator adapted to move the movable wall between its first and second position;
an imaging sensor positioned to image the contents of the channel at the point of the movable wall through the transparent window.

2. The analytical toilet of claim 1 wherein the transparent wall is positioned on the opposite side of the channel from the movable side.

3. The analytical toilet of claim 1 wherein the transparent wall is part of the movable side.

4. The analytical toilet of claim 1 wherein the imaging sensor comprises a microscopic lens.

5. The analytical toilet of claim 1 wherein the imaging sensor is positioned below the channel.

6. The analytical toilet of claim 1 further comprising a light source illuminating the imaging section of the channel.

7. The analytical toilet of claim 6 wherein the light source is behind the transparent window.

8. The analytical toilet of claim 1 wherein the movable wall comprises a flexible diaphragm.

9. The analytical toilet of claim 8 wherein the flexible diaphragm comprises a polymer.

10. The analytical toilet of claim 8 wherein the flexible diaphragm comprises a silicone-based polymer.

11. The analytical toilet of claim 1 wherein the transparent window comprises glass.

12. The analytical toilet of claim 1 wherein the transparent window is a lens for the imaging sensor.

13. The analytical toilet of claim 1 wherein the transparent window comprises a polymer.

14. The analytical toilet of claim 1 wherein the channel is part of a manifold system in fluid communication with the bowl.

15. The analytical toilet of claim 14 wherein the manifold comprises a plurality of fluid channels.

16. The analytical toilet of claim 14 wherein the manifold comprises a plurality of digitally controlled valves.

17. The analytical toilet of claim 14 wherein the manifold is adapted to supply different fluids to the channel.

18. The analytical toilet of claim 17 wherein the manifold supplies one or more of water, reagents, dyes, cleaners, diluents, buffers, cleansers, and rinse solutions.

19. The analytical toilet of claim 18 wherein the water is deionized water.

* * * * *